United States Patent
Hahn et al.

(10) Patent No.: US 7,044,940 B1
(45) Date of Patent: May 16, 2006

(54) STORAGE CONTAINER FOR A SUSPENSION USED FOR MEDICAL PURPOSES

(75) Inventors: Rainer Hahn, Tübingen (DE); Uwe Grotz, Löchgau (DE); Ulrich Prager, Abstatt (DE)

(73) Assignee: Dürr Dental GmbH & Co. KG, Biztigheim-Bissingen (DE)

( * ) Notice: Subject to any disclaimer, the term of this patent is extended or adjusted under 35 U.S.C. 154(b) by 0 days.

(21) Appl. No.: 09/547,156

(22) Filed: Apr. 11, 2000

(30) Foreign Application Priority Data

Apr. 11, 1999 (DE) .......................................... 199 16 154

(51) Int. Cl.
*A61B 7/00* (2006.01)
*B65D 83/10* (2006.01)

(52) U.S. Cl. ........................................ 604/408; 206/363
(58) Field of Classification Search ......... 604/403–408, 604/262; 128/DIG. 24; 383/35, 6, 33, 210.1; 220/62.22; 206/363
See application file for complete search history.

(56) References Cited

U.S. PATENT DOCUMENTS

| | | | | |
|---|---|---|---|---|
| 2,891,700 A | * | 6/1959 | Maynard ..................... | 222/92 |
| 3,746,001 A | * | 7/1973 | Ralston, Jr. ................. | 215/247 |
| 4,795,457 A | * | 1/1989 | Cooney ...................... | 604/408 |
| 5,395,365 A | * | 3/1995 | Weiler et al. ........ | 128/DIG. 24 |
| 5,941,421 A | * | 8/1999 | Overman et al. ........... | 222/105 |
| 5,941,866 A | * | 8/1999 | Niedospial, Jr. ............ | 604/403 |

* cited by examiner

*Primary Examiner*—Angela D. Sykes
*Assistant Examiner*—Leslie Deak

(57) ABSTRACT

A storage container (1) for a suspension used for medical purposes, in particular for ultrasonically assisted treatment of periodontitis, dental cleaning or dental preparation, comprises a flexible pouch (2), the interior of which is accessible via a charging and discharging nozzle (5). Situated in the interior of the pouch (2) is a distance element (6), in which a groove system (8, 9, 10) is incorporated. The groove system communicates with the interior of the charging and discharging nozzle (5). When the pouch (2) of said storage container (1) is pressed flat during removal of the suspension it contains, the opposing sides (3, 4) of the pouch (3) are applied during the final phase of emptying against the distance element (6). The groove system (8, 9, 10) contained in the latter however remains clear and forms a path, via which even the last residues of the suspension may be reliably removed from the pouch (2).

7 Claims, 2 Drawing Sheets

STORAGE CONTAINER FOR A SUSPENSION USED FOR MEDICAL PURPOSES

Figure 1:
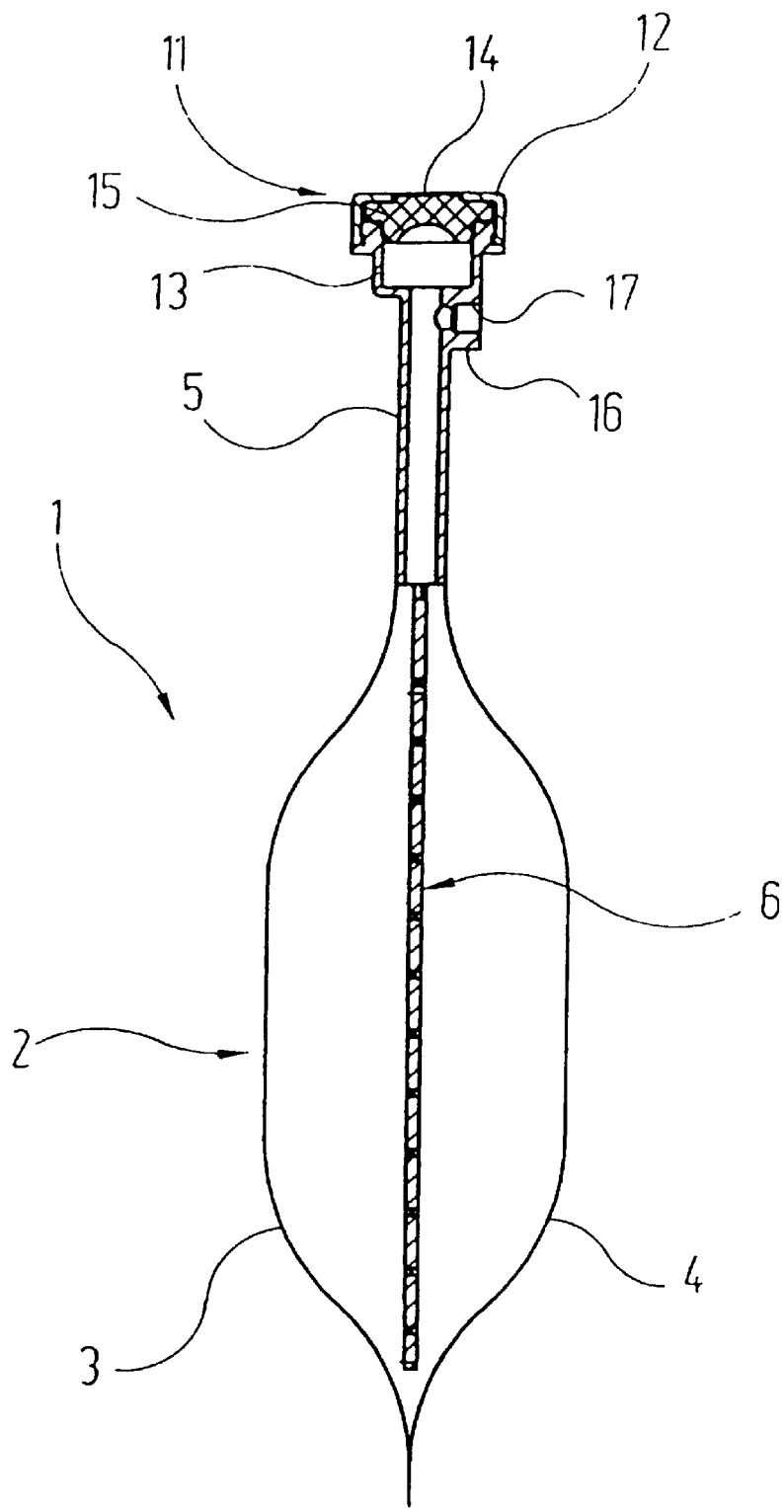

The invention relates to a storage container for a suspension used for medical purposes, comprising a flexible pouch, a charging and discharging nozzle leading to the interior of the pouch, and a sealing device for sealing the charging and discharging nozzle.

A special, particularly preferred area of application of such storage containers is their use in sonic or ultrasonic treatment instruments for treating periodontitis or for minimally invasive dental polishing or dental preparation, peri-implantitis therapy as well as for root canal treatments or dental repair. The suspension in said case possesses a consistency and components which support the action of the treatment instrument oscillating at sonic or ultrasonic frequency. Such suspensions have to be manufactured under hygienic or sterile conditions in the factory and then despatched and stored in a storage container until they are used in the sonic or ultrasonic treatment instrument. There, they are connected to a flow path for the suspension, which terminates in the vicinity of the oscillating instrument. The contents of the pouch are sucked out with the aid of a pump, whereby the opposing walls of the pouch move progressively towards one another.

In known storage containers of the type described initially, it was possible for the opposing walls of the pouch during the final discharge phase to come into local contact with one another and "stick", thereby impeding the further passage of suspension and hence preventing complete emptying of the pouch.

The object of the invention is to refine a storage container of the type described initially in such a way that enables complete emptying of the pouch.

Said object is achieved according to the invention in that disposed in the interior of the pouch is a distance element, in which at least one groove system communicating with the charging and discharging nozzle is incorporated.

In a storage container according to the invention, during the final phase of the discharge operation the opposing, flexible walls of the pouch are applied against the surfaces of the distance element without, however, penetrating into the grooves of the groove system. Said groove systems therefore remain clear as flow paths for the suspension up to the end of the discharge operation so that the suspension may be reliably removed from all regions of the pouch.

The distance element is preferably a flat plate which carries a groove system on each of its opposite sides. The distance element inside the pouch therefore takes up only a very low volume, which is not available as a charging volume for the suspension. The groove systems provided on either side of the distance element allow reliable removal of the suspension from both sub-chambers, into which the distance element subdivides the interior of the pouch.

It has proved particularly successful when the groove system has a herringbone configuration and comprises a central groove leading to the charging and discharging nozzle as well as two sets of lateral grooves leading to the central groove. In said manner, during the final phase of emptying the pouch the suspension may be reliably extracted from all regions of the pouch.

The sealing device may comprise a cap, which is fastenable on the end of the charging and discharging nozzle and designed in one region of its end face as a pierceable membrane, wherein a sealing membrane of elastomeric material is braced between the cap and the charging and discharging nozzle. The sealing device refined in said manner is a guarantee closure, the integrity of which provides a guarantee of the quality and condition of the suspension contained in the pouch. To connect the storage container to the ultrasonic treatment apparatus, a needle is punched through the thin membrane of the cap as well as through the elastic sealing membrane.

In a preferred embodiment of the invention, the pierceable membrane and/or the sealing membrane are made of a material which hermetically re-seals after the needle is withdrawn. It is then also possible for a partially used pouch to be removed from the treatment instrument, stored temporarily and later reutilized and pierced again for another treatment session. Said procedure may, if need be, even be repeated several times.

It is advantageous when the charging and discharging nozzle comprises a lateral, sealable charging projection. If the suspension is introduced through said charging projection into the interior of the pouch prior to provision of the sealing device, air may escape from the pouch through the open end of the charging and discharging nozzle. This facilitates total charging of the pouch with the suspension.

Figure 2:
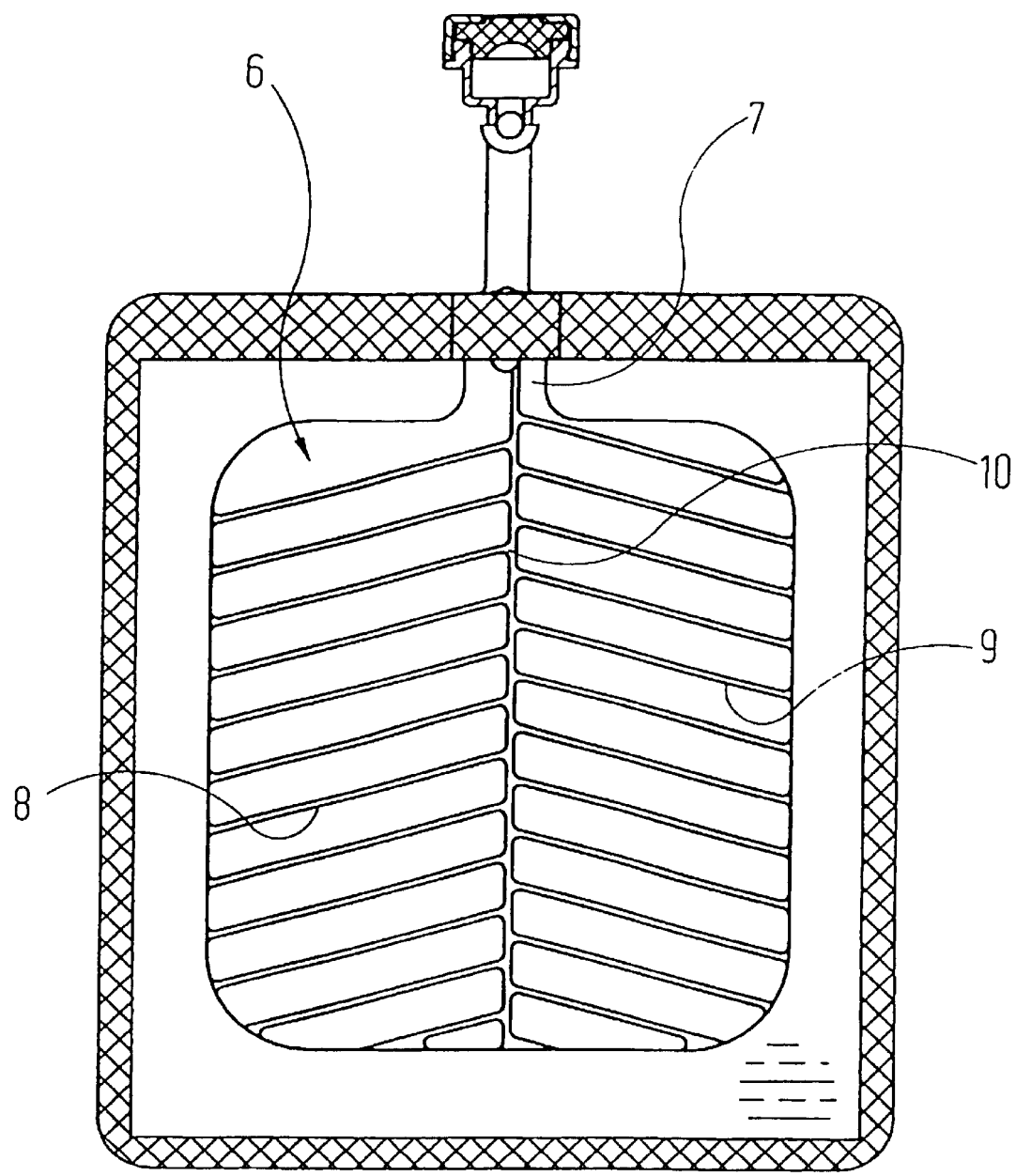

There now follows a detailed description of an embodiment of the invention with reference to the drawings; said drawings show:

FIG. 1 a section through a storage container for a suspension used for dental treatment;

FIG. 2 the side view of the storage container of FIG. 1, partially in section.

The storage container denoted as a whole in the drawings by the reference character 1 is used for hygienic or sterile storage of an aqueous suspension, which is utilized in particular for ultrasonic treatment of periodontitis, dental cleaning or minimally invasive dental preparation. The storage container 1 comprises a pouch 2, which is formed by welding together two flexible foils 3, 4 at their edges. The interior of the pouch 2 for containing the suspension is accessible via a charging and discharging nozzle 5.

Provided in the centre plane of the pouch 2 is a distance element 6, which is made of relatively rigid material and takes the form of a narrow plate. It is connected by a projection 7 to the charging and discharging nozzle 5.

Both surfaces of the distance element 6 comprise a herringbone system of grooves 8, 9, 10. A central groove 10 penetrates the entire distance element 6 from the bottom to the top and communicates with the interior of the charging and discharging nozzle 5. Two sets of lateral grooves 8, 9 lead obliquely from the outside into the central groove 10; they are set in such a way relative to the central groove 10 that they promote a flow from outside in towards the central groove 10 and, in the latter, —in the drawings—up towards the charging and discharging nozzle 5.

The charging and discharging nozzle 5 carries at its top end a sealing device 11. The latter comprises a pot-shaped plastic cap 12, which is clipped or welded onto a head 13 of the charging and discharging nozzle 5. The end face of the plastic cap 12 is kept very thin in the central region and here forms a pierceable membrane 14.

A sealing membrane 15 of elastomeric material is braced between the plastic cap 12 and the head 13 of the charging and discharging nozzle 5.

Below the head 13, a charging projection 16 branches off from the charging and discharging nozzle 5 and has a through-bore 17 sealable in a suitable manner.

The described storage container is utilized as follows:

In the factory, the suspension is introduced under hygienic or sterile conditions into the pouch 2 of the storage container 1 via the through-bore 17 of the charging projection 16. The sealing device 11 in said case has not yet been provided, with the result that air may escape from the pouch 2 through the open head 13. After charging, the sealing device 11 is provided by clipping or welding on the cap 12, into which the sealing membrane 15 has been inserted. In said form, the storage container 1 may be despatched and stored at the dental surgery.

When required, such a storage container 1 is connected to an ultrasonic treatment instrument. This is effected by punching a needle, which forms part of the ultrasonic treatment instrument, through the membrane 14 of the cap 12 and through the sealing membrane 15. The suspension situated in the interior of the pouch 2 is then extracted from the pouch 2 by a pump of the ultrasonic treatment instrument and fed through the charging and discharging nozzle 5 and the inserted needle to the ultrasonic treatment instrument.

Complete emptying of the pouch 2 is guaranteed by the distance element 9. It namely prevents the two opposing foils 3, 4, from which the pouch 2 is made, from being able to come into local contact with one another during the final extraction phase, thereby impeding further removal of the suspension. Instead, said final extraction phase the two foils 3, 4 are applied against the opposing surfaces of the distance element 6. The pattern of grooves 8, 9, 10, which are contained in said surfaces and into which the foils 3, 4 do not penetrate during said operation, guarantees that the suspension is reliably carried away from all regions of the pouch 2 towards the charging and discharging nozzle 5.

Once all of the suspension has been removed from the storage container 1, the latter is replaced by a fresh, full storage container.

What is claimed is:

1. A storage container for a suspension used for medical purposes, comprising a flexible pouch formed by two flexible walls sealingly connected at their peripheral rims, a sealing line defining a central plane of the pouch, a charging and discharging nozzle leading to the interior of the pouch, and a sealing device for sealing the charging and discharging nozzle, wherein disposed in an interior of the pouch (2) is a distance element (6), in a form of a noncorrugated flat plate having two spaced parallel flat surfaces arranged on said central plane and having two opposing plane surfaces which carry a groove system (8, 9, 10) comprising a plurality of grooves.

2. A storage container as claimed in claim 1, wherein the groove system (8, 9, 10) has a herringbone configuration and comprises a central groove (10) leading to the charging and discharging nozzle (5) and two sets of lateral grooves (8, 9) leading to the central groove (10).

3. A storage container as claimed in claim 2, wherein the two sets of lateral grooves (8, 9) are displaced to one another.

4. A storage container as claimed in claim 1, wherein the sealing device (11) comprises a cap (12), which is fastened on an end of the charging and discharging nozzle (5) and designed in one region of its end face as a pierceable membrane (14), and wherein a sealing membrane (15) of elastomeric material is braced between the cap (12) and the charging and discharging nozzle (5).

5. A storage container as claimed in claim 1, wherein the charging and discharging nozzle (5) comprises a lateral sealable charging projection (16).

6. A storage container as claimed in claim 1, wherein the flexible pouch has edges and a rim of the flat plate is essentially parallel to the edges of the flexible pouch.

7. A storage container as claimed in claim 1, wherein the two plane surfaces of the distance element (6) are essentially co-planar to the central plane of the pouch.

* * * * *